United States Patent [19]
Pitsch et al.

[11] Patent Number: 5,986,084
[45] Date of Patent: Nov. 16, 1999

[54] RIBONUCLEOSIDE-DERIVATIVE AND METHOD FOR PREPARING THE SAME

[76] Inventors: Stefan Pitsch, Regensorferstrasse 45, 8049 Zürich; Patrick A. Weiss, Luegislandstrasse 241, 8051 Zürich; Luzi Jenny, Rotwandstrasse 65, 8004 Zürich, all of Switzerland

[21] Appl. No.: 08/965,780

[22] Filed: Nov. 7, 1997

[30] Foreign Application Priority Data

Aug. 18, 1997 [CH] Switzerland ............... 01931/97

[51] Int. Cl.$^6$ ................................... C07H 21/02
[52] U.S. Cl. ............... 536/25.31; 536/25.3; 536/25.34; 536/26.7; 536/26.74; 536/26.8; 536/26.9
[58] Field of Search ............... 536/25.3, 25.31, 536/25.34, 26.7, 26.74, 26.8, 26.9

[56] References Cited

PUBLICATIONS

MacLeod et al., "Mass Spectroscopy of Cytokinin Metabolites. Per(trimethylsilyl) and Permethyl Derivatives of Glucosides of Zeatin and 6–Benzylaminopurine," *J. Organic Chemistry*, 41(25), 3959–3967 (Dec. 10, 1976).

Nagatsugi et al., "2–Aminopurine Derivatives with C6–Substituted Olefin as Novel Cross–Linking Agents and the Synthesis of the Corresponding β–Phosphoramidite Precursors," *Tetrahedron*, 53(9), 3035–3044 (Mar. 3, 1997).

Boons et al., "Use of (Phenyldimethylsilyl)methoxxymethyl and (Phenyldimethylsilyl)methyl Ethers as Protecting Groups for Sugar Hydroxyls," *Tetrahedron Letters*, 31(15), 2197–2200 (1990).

Usman et al. "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethionine tRNA" Journal of the American Chemical Society, vol. 109, pp. 7845–7854, (Sep. 12, 1987).

*Primary Examiner*—L. Eric Crane
*Attorney, Agent, or Firm*—Kubovcik & Kubovcik

[57] ABSTRACT

The ribonucleoside-derivatives serve for the synthesis of ribonucleic acids and comprise a triple substituted silyloxymethyl-group as a protection-group on the oxygen atom in 2'-position. The ribonucleoside-derivatives may be suitably protected on the nucleo-base and on the oxygen in 5'-position also. The new protection-groups in 2'-O-position are superior to conventional such protection-groups as they are not subject to isomerization and give higher coupling yields. The general formula of the ribonucleoside-derivative is:

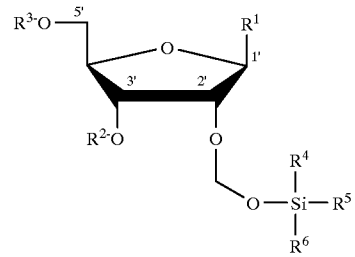

whereby $R^1$ is a base of the purine- or pyrimidine-family or a derivative of such a base, $R^2$ is a proton or a substituted derivative of phosphonic acid, $R^3$ is a proton or a suitable protection-group, $R^4$, $R^5$, $R^6$ are advantageously three identical or different alkyl- or aryl-substituents which together comprise between 6 and 30 carbon atoms.

14 Claims, 2 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligoribonucleotide"

(xi) SEQUENCE DESCRIPTION: SEQ ID NO:1:

UUUUUUUUUU UUUUUUUUUU                                           20

(2) INFORMATION FOR SEQ ID NO:2:

(i) SEQUENCE CHARACTERISTICS:
        (A) LENGTH: 35 base pairs
        (B) TYPE: nucleic acid
        (C) STRANDEDNESS: single
        (D) TOPOLOGY: linear

(ii) MOLECULE TYPE: other nucleic acid
        (A) DESCRIPTION: /desc = "oligoribonucleotide"

(xi) SEQUENCE DESCRIPTION: SEQ ID NO:2:

GCUCGUCUGA UGAGUCCGUG AGGACGAAAG ACCGU               35

RIBONUCLEOSIDE-DERIVATIVE AND METHOD FOR PREPARING THE SAME

FIELD OF THE INVENTION

The invention is in the field of nucleic acid chemistry and concerns a ribonucleoside-derivative and a method for preparing the ribonucleoside-derivative. The inventive ribonucleoside-derivative is characterized by a protection-group on the oxygen atom in 2'-position of the ribose-unit and is especially suitable for machine synthesis of ribonucleic acids.

BACKGROUND OF THE INVENTION

The present invention is connected to the chemical synthesis of ribonucleic acids (ribo-oligonucleotides, RNA), especially to the machine synthesis of such oligomers as well as to the synthesis of structurally related derivatives of such oligomers.

Pure oligonucleotides of a defined sequence prepared in a chemical synthesis are e.g. used in the field of structural analysis of unit crystals by means of X-ray diffraction or by means of nuclear magnetic spectroscopy. This kind of research contributes to the understanding of biological processes on a molecular level and among other things makes, development of novel therapy concepts possible. Ribonucleic acids constituting a central biological class of compounds (messenger-RNA, transfer-RNA, ribosomal-RNA) are interesting objects for medical chemistry. In this context the availability of assays for fast and reliable testing of compounds potentially interacting with RNA is highly desirable. By chemical synthesis (opposed to production using enzymes, organisms etc.) of such oligonucleotides for testing, introduction of purposeful modifications becomes possible which modifications e.g. allow simple quantification of a desired interaction or make a specific interaction accessible to precise examination.

Natural and modified RNA-oligonucleotides also find use as tools for selective recognition and/or selective modification of RNA- and DNA-oligonucleotide-sequences and other compounds (aptamers and ribozymes). Improvements to be achieved in the chemical synthesis of such compounds could make the introduction of purposeful modifications possible and thus considerably extend the field of application of the types of compounds as described above in medical diagnostics and therapy.

All known methods for chemical synthesis of RNA-oligonucleotides and derivatives thereof are related to concepts which have been very successfully developed for the synthesis of DNA-oligonucleotides (2'-desoxyribonucleic acids, opposed to RNA which comprises a hydroxy-group in the 2'-position). The machine synthesis of DNA- and RNA-oligonucleotides is normally based on a protected nucleoside-derivative immobilized on a solid phase to which further protected nucleoside-derivatives are coupled in steps of one synthesis cycle each until the desired length of chain is achieved. Finally the built-up sequence is freed of all protection-groups and separated from the solid phase.

Ribonucleoside-derivatives for application in the chemical synthesis of ribonucleic acids comprise a D- or L-ribose-unit and have the following general structural formula:

whereby $R^1$ is a base of the purine- or pyrimidine-family or a derivative of such a base, $R^2$ is a proton or a substituted derivative of phosphonic acid, $R^3$ is a proton or a protection-group for the oxygen atom in 5'-position, X is a protection-group for the oxygen atom in 2'-position.

The protection-group X for the oxygen atom in 2'-position is to fulfil substantially the following conditions:

The introduction of the protection-group has to be as simple as possible and has to yield uniform compounds which are as free from isomerization products as possible.

The protection-group has to be absolutely stable under the coupling conditions.

The protection-group has to have a structure which allows high coupling yields.

The protection-group has to be completely removable without decomposition or chemical change of the compound to be prepared.

The protection-groups which have been used so far for the 2'-position substantially belong to the three following types. A number of further such protection-group types exist. However, they have not been completely successful for different reasons.

a) Acid-sensitive 2'-O-acetal-protection-groups [1]:

EXAMPLE: X=

This type of protection-group is easily introduced and the chemicals required for establishing such protection-groups as well as the nucleosides carrying them are commercially available. Disadvantages of the protection type are the facts that the protection-groups are not completely stable on synthesis of the chains, that using such protected nucleoside-derivatives only moderate coupling yields are achievable and that isomerization on de-protection is possible.

b) Photo-sensitive 2'-O-ortho-nitrobenzyloxymethyl-protection-groups [2]:
Example: X=

3

This type of protection-group is easily introduceable, de-protecting is completely orthogonal and good coupling yields are achievable. Disadvantages of this type of protection-group are the facts that complete de-protecting is sometimes not possible and that the chemicals necessary for establishing the protection-groups are not available on the market.

c) Fluoride-sensitive 2'-O-silyl-protection-groups [3]:
Example: X=

4

This type of protection-group is easily and completely removable (de-protecting), the application is established and the necessary chemicals are available on the market. Disadvantages of this type of protection-groups are the facts that they are difficult to be introduced, that the ribonucleoside-derivatives prepared by introducing the protection-group contain isomers and that only moderate coupling yields are achievable.

The object of the invention is to create ribonucleoside-derivatives comprising a protection-group in 2'-O-position, whereby the inventive nucleoside-derivatives unite the advantages of nucleoside-derivatives with known protection-groups as mentioned above under b) and c) (good introduceability of the protection-group, good stability of the protection-group, high coupling yields and simple de-protecting) but do not show the known disadvantages, in particular no isomerization on introducing and on removing the protection-group.

The use of the inventive ribonucleoside-derivatives protected with a 2-O-protection-group are to allow a chemical synthesis of oligo-ribonucleic acids and of structurally related derivatives thereof with a substantially higher yield and with higher purity than is possible with known units of this kind and therefore, are to make synthesis of substantially longer chains possible.

Furthermore, it is the object of the invention to provide a method for preparing the inventive ribonucleoside-derivatives.

SHORT DESCRIPTION OF THE INVENTION

The inventive ribonucleoside-derivatives contain a 2'-O-silyloxymethyl-protection-group (structural formula 5), whereby the silicon atom of the silyloxyethyl-group additionally comprises three identical or different substituents. These three substituents are advantageously alkyl- or aryl-substituents. The three alkyl- or aryl-groups can also be aryl-alkyl-combinations, can be substituted with heteroatoms and/or can be connected to each other in ring-form. It shows that the three substituents of the 2'-O-silyloxymethyl-group can together comprise between 6 and 30 C-atoms.

X=

5

As an example the three substituents of the silicon atom in the 2'-O-silyloxymethyl-protection-group are three isopropyl-groups (structural formula 6)

X=

6

Due to the acetal nature of the bond between nucleoside and protection-group in the inventive 2'-O-protected ribonucleoside-derivative no migration of the protection-group to a different position inside the ribonucleoside-derivative, in particular no migration to the neighboring 3'-O-position can occur. Such isomerization is an important and well known problem in the synthesis of the conventional 2'-O-silyl-substituted RNA-units (type of protection-group c), see above) [6, 7] which problem is solved for the inventive ribonucleoside-derivatives by the new protection-group.

The 2'-O-silyloxymethyl-protection-group is less bulky because it is linked to the ribose unit via the relatively small and sterically undemanding methene-unit. This, in opposition to units with the known considerably more bulky trialkylsilyl-groups bonded directly to the 2'-oxygen atom (types of protection-groups c), see above) reduces steric hinderance of the reaction center for the coupling reaction (3'-O-phosphor atom) and thus increases the coupling yield. When building chains starting from the inventive units yields of more than 98% can be expected, compared to yields of less than 97% as common when starting from known units.

As the difficulties of the chain formation caused by steric hindrance are greatly reduced by the methoxy-spacer of the protection-group of the inventive ribonucleic-acid-unit steric effects can be substantially neglected when choosing the three substituents of the silicon atom. Instead, additional criteria, in particular stability against acid and/or base can be taken into consideration. Furthermore, the protection-group can be adapted to a higher degree to the requirements of a specific case.

The separation of the 2'-O-silyloxymethyl-protection-group (de-protecting) can be carried out substantially under the same conditions as the separation of the conventional 2'-O-Silyl-protection-groups, i.e. by treatment with fluoride-ions or fluorosilicic acid. This de-protecting reaction is known to users of ribonucleic-acid-units as a well established and problem-free reaction and the fact that this reaction can be taken over for de-protecting the inventive units is a further advantage of these units.

For preparing the inventive compounds an efficient, cheap and simple method of synthesis is used, which method yields products substantially free of unwanted isomers (purity >99.8%). By using the inventive ribonucleoside-derivatives, synthetically prepared oligo-nucleic-acids with chains (more than 40 nucleotide units) longer than previously possible become available and RNA-oligonucleotides in generally larger amounts (1–20 mg per individual synthesis) and in uniform, chemically pure form (over 90% in weight of the compound with the desired structure) become available for many interesting applications.

DETAILED DESCRIPTION OF THE INVENTION

The reaction 7→8→9 shows an example of the synthesis of a compound according to the invention. This synthesis starts from nucleosides 7 which are already partly protected. A cyclic 2',3'-di-O-dialkyl-(or diaryl-)stannyl derivative (e.g. dibutyl-stannyl-derivative) is synthesized under alkaline conditions, in the presence of an excess of a tertiary amine base which derivative reacts with a tri(alkyl- and/or aryl)-substituted silyloxy-methylchloride to form the ribonucleoside-derivative 8. This is then converted to the corresponding phosphoramidite 9 under established conditions [4].

As mentioned above the substituents $R^4$, $R^5$ and $R^6$ of the 2'-O-silyloxymethyl-protection-group which protection-group distinguishes the inventive nucleoside-derivative, are identical or different alkyl- or aryl-substituents or combinations of these and can also be substituted with heteroatoms and/or be connected to each other forming ring structures. The three substituents together comprise advantageously between 6 and 30 carbon atoms. They are e.g. three isopropyl-groups.

The components and other substituents of the initial product which is not yet protected in 2'-O-position and of the protected product correspond precisely to the components and substituents which are used in conventional synthesis methods for preparing protected ribonucleoside-derivatives.

The protection-group $R^3$ in 5'-O-position is e.g. a monomethoxytrityl- or dimethoxytrityl-group or a different, suitable group which is removed from the growing sequence during chain building such freeing a bonding position for coupling the next unit to be added to the chain.

The base-component $R^1$ of the ribonucleoside-derivative is a base of the purine- or pyrimidine family, e.g. one of the five nucleobases adenine, cytosine, thymine, uracile, guanine or a derivative thereof. It can be protected by an acyl-substituent which can be removed after chain creation.

The derivative of phosphonic acid in the 3'-O-position is an N,N- and O-substituted phosphoramidite group, whereby the N-substituents $R^7$ and $R^8$ are alkyl- or aryl-groups which can be further substituted and/or cyclically connected to each other. $R^7$ and $R^8$ are e.g. isopropyl-groups. By activating the nitrogen of the disubstituted amino-group the phosphorus center is activated for coupling the unit to a growing chain.

The O-substituent $R^9$ of the phosphoramidite-group is an alkyl- or aryl-substituent (possibly substituted by heteroatoms) which is removed after chain creation.

One skilled in the art of oligonucleotide-synthesis knows the principles of the synthesis of the inventive ribonucleoside-derivatives and their coupling to form oligonucleotides. For further illustration of the simplicity of the synthesis and the superiority of the inventive units for the synthesis of ribonucleic acids several examples follow.

EXAMPLE 1

The synthesis of the uridine-unit 1-{3'-O-[(2-cyanoethoxy)(diisopropylamino)-phosphino]-5'-O-[4,4'-dimethoxytrityl]-2'-O-[triisopropyl-silyloxymethyl]-β-D-ribofuranosyl}-uracile 12 was carried out starting from 1-[5'-O-(4,4'-dimethoxytrityl)-β-D-ribofuranosyl]-uridine 10 and carried out via the intermediate product 11: 1-[5'-O-(4,4'-dimethoxytrityl)-2'-O-(triisopropyl-silyloxymethyl)-β-D-ribofuranosyl]-uracile.

The protected ribonucleoside-derivative 11 was purified to an isomerically pure form by means of simple chromatography on silica gel.

EXAMPLE 2

EXAMPLE 3

Procedure for the preparation of (Chloromethoxy) (triisopropyl)-silane (according to [8])

A suspension of 0.1 mol para-formaldehyde in 0.1 mol ethanethiol was treated with 1 drop 10N aequous NaOH-solution and stirred at room temperature until a clear solution was obtained. After stirring for 1 hour at 50° C., 50 ml $CH_2Cl_2$ and 0.2 mol imidazole, followed by 0.09 mol $(i-Prop)_3SiCl$ were added. The resulting suspension was stirred at room temperature overnight and diluted with 400 ml hexane. After addition of 250 ml aequous 2M $NaH_2PO_4$-solution, stirring and phase separation, the organic phase was evaporated. The residue was dissolved in 250 ml $CH_2Cl_2$, treated with 0.09 mol sulfurylchloride, stirred 1 hour at room temperature, evaporated and distilled in vacuo. The product was obtained as colourless, viscous oil (yield: 90%).

Boiling point: 50° C. (0.1 torr). $^1$H-NMR (300 MHz, CDCl$_3$): 1.08–1.10 (m, 21 H, CH$_3$ and CH from (i-Prop)$_3$Si—); 5.66 (s, 2H, CH$_2$Cl).

EXAMPLE 4

Procedure for the preparation of the 2'-O-[(i-Prop)$_3$SiOCH$_2$]-protected nucleosides 5–8

BASE =
1 N$^6$-Benzoyl-adenine
2 N$^4$-Benzoyl-cytosine
3 N$^2$-Isobutyryl-guanine
4 Uracile BASE =
5 N$^6$-Benzoyl-adenine
6 N$^4$-Benzoyl-cytosine
7 N$^2$-Isobutyryl-guanine
8 Uracile A solution of 10 mmol 5'-O-dimethoxytritylated, eventually base protected nucleoside 1–4 (preparation according to [9]) in 40 ml 1,2-dichloroethane was treated at room temperature first with 50 mmol N-ethyl-N,N-diisopropylamine and then with 11 mmol dibutyltin dichloride. After stirring for 15 minutes at room temperature, the reaction mixture was heated to 80° C., treated with 13 mmol (chloromethoxy) (triisopropyl)-silane and stirred for 30 to 90 minutes at 80° C., until only traces of starting material could be detected by thin-layer-chromatography. After cooling to room temperature, the reaction mixture was diluted with 200 ml CH$_2$Cl$_2$, 200 ml aqueous saturated NaHCO$_3$-solution were added and the resulting mixture was stirred for 20 minutes. The cloudy organic phase obtained after phase separation was dried over MgSO$_4$ and filtered through a pad of Celite. The residue, obtained after concentration, was subjected to column-chromatography on 100 g of silica gel using as eluent hexane/ethyl acetate mixtures, containing 2% NEt$_3$. The products were obtained as colorless foams.

N$^6$-Benzoyl-9-[5'-O-(4,4-dimethoxytrityl)-2'-O-([(triisopropysilyl)oxy]methyl))-β-D-ribofuranosyl]adenine (5):

Yield: 45–55%.

TLC: R$_f$0.60 (AcOEt/hexane 7:3). $^1$H-NMR (300 MHz, CDCl$_3$): 1.03 −1.15 (m, 21H, CH$_3$ and CH from (i-Prop)$_3$Si—); 3.08 (d, J=3.7, 1H, HO—C(3'), disappears upon treatment with D$_2$O); 3.40 (dxd, J=10.2, 4.1, 1H, H—C(5')); 3.62 (dxd, J=10.2, 3.5 Hz, 1H, H'—C(5')); 3.78 (s, 6H, CH$_3$O—Ar); 4.31 (q, J=4.0, 1H, H—C(4')); 4.57 (br. q, J Å 4, 1H, H—C(3'), changes to t upon treatment with D$_2$O); 4.98 (br. t, J Å 5, 1H, H—C(2')); 4.98 and 5.16 (two d, J=4.7, 2H, OCH$_2$O); 6.24 (d, J=5.6, 1H, H—C(1')); 6.79 −6.83 (m, 4H, arom. H); 7.21–7.65 (m, 12H, arom. H); 8.01–8.04 (m, 2H, arom. H); 8.21 (s, 1H, H—C(2)); 8.73 (s, H—C(8)); 8.97 (br, s, 1H, NH—C(6), disappears upon treatment with D$_2$O).

N$^4$-Benzoyl-1-[5'-O-(4,4-dimethoxytrityl)-2-O-([(triisopropylsilyl)oxy]methyl))-β-D-ribofuranosyl] cytosine (6)

Yield: 50–60%

TLC: R$_f$0.65 (AcOEt/hexane 7:3). $^1$H-NMR (300 MHz, CDCl$_3$): 1.02–1.18 (m, 21H, CH$_3$ and CH from (i-Prop)$_3$Si—); 3.34 (d, J=8.3, 1H, HO—C(3'), disappears upon treatment with D$_2$O); 3.55 (dxd, J=11.6, 3.0, 1H, H—C(5')); 3.62 (dxd, J=11.6, 3.0 Hz, 1H, H'—C(5')); 3.83 (s, 6H, CH$_3$O—Ar); 4.12 (dxt, J=8.3, 3.0, 1H, H—C(4')); 4.28 (d, J=5.4, 1H, H—C(2')); 4.41 (txd, J=8.3, 5.4, 1H, H—C(3'), changes to dxd upon treatment with D$_2$O); 5.19 and 5.30 (two d, J=4.6, 2H, OCH$_2$O); 6.01 (s, 1H, H—C(1')); 6.84 −6.92 (m, 4H, arom. H); 7.23–7.62 (m, 13H, 12 arom. H and H—C(5)); 7.85–7.92 (m, 2H, arom. H); 8.54 (d, J=6.5, 1H, H—C(6)); 8.55, (br. s, 1H, HN—C(4), disappears upon treatment with D$_2$O).

N$^3$-Isobutyryl-9-[5'-O-(4,4'-dimethoxytrityl)-2'-O-([(triisopropylsilyl)oxy]methyl))-β-D-ribofuranosyl] guanine (7)

Yield: 80–90%.

TLC: R$_f$0.50 (AcOEt/hexane 7:3). $^1$H-NMR (300 MHz, CDCl$_3$): 0.66, 0.87 (2d, J=6.9, 6H, CH(CH$_3$)$_2$); 1.02–1.11 (m, 21H, CH$_3$ and CH from (i-Prop)$_3$Si—); 1.49 (hept, J=6.9, 1H, CH(CH$_3$)$_2$); 3.02 (d, J=1.9, 1H, HO—C(3'), disappears upon treatment with D$_2$O); 3.00 (dd, J=3.1, 10.6, 1H, H—C(5')); 3.54 (dd, J=2.1, 10.6, 1H, H'—C(5')); 3.76, 3.77 (2s, 2×3H, OCH$_3$); 4.22 (br. q, J Å 2, 1H, H—C(4')); 4.57 (m, 1H, H—C(3'), changes to dxd upon treatment with D$_2$O); 4.95, 5.14 (2d, J=4.7, 2H, OCH$_2$O); 5.08 (dd, J=5.1, 7.2, 1H, H—C(2')); 5.89 (d, J=7.2, 1H, H—C(1')); 6.77–6.82 (m, 4H, arom. H); 7.21–7.57 (m, 9H, arom. H); 7.77 (br. s, NH—C(2)); 7.79 (s, 1H, H—C(8)); 11.95 (br. s, 1H, H—N(1), disappears upon treatment with D$_2$O).

1-[5'-O-(4,4'-dimethoxytrityl)-2'-O-([(triisopropylsilyl)oxy]methyl))-β-D-ribofuranosyl]uracile (8)

Yield: 45–55%.

TLC: R$_f$0.75 (AcOEt/hexane 3:2). $^1$H-NMR (300 MHz, CDCl$_3$): 1.02–1.18 (m, 21H, CH$_3$ and CH from (i-Prop)$_3$Si—); 3.17 (d, J=5.5, 1H, HO—C(3'), disappears upon treatment with D$_2$O); 3.51 (d, J=2.5, 2H, H—C(5') and H'—C(5')); 3.80 (s, 6H, CH$_3$O—Ar); 4.12 (dxt, J=5.5, 2.5, 1H, H—C(4')); 4.28 (dxd, J=3.2, 5.5, 1H, H—C(2')); 4.47 (q, J=5.5, 1H, H—C(3'), changes to t upon treatment with D$_2$O); 5.04 and 5.23 (two d, J=5.0, 2H, OCH$_2$O); 5.30 (d, J=7.9, 1H, H—C(5)); 6.03 (d, J=3.2, 1H, H—C(1')); 6.80 −6.88 (m, 4H, arom. H); 7.24–7.42 (m, 9H, arom. H); 7.94 (d, J=7.9, 1H, H—C(6)); 8.56, (br. s, 1H, H—N(3), disappears upon treatment with D$_2$O).

EXAMPLE 5

Procedure for the preparation of the Phosphoramidites 9–12

BASE =
5 N⁶-Benzoyl-adenine
6 N⁴-Benzoyl-cytosine
7 N²-Isobutyryl-guanine
8 Uracile BASE =
9 N⁶-Benzoyl-adenine
10 N⁴-Benzoyl-cytosine
11 N²-Isobutyryl-guanine
12 Uracile A solution of 10 mmol protected nucleoside 5–8 in 30 ml CH$_2$Cl$_2$ was treated consecutively with 20 mmol N-ethyl-N,N-diisopropylamine and 20 mol chloro(2-cyanoethoxy)(N,N-diisopropylamino)phosphine [4]. After stirring for 3 h at room temperature, the reaction mixture was subjected to columnchromatography on 150 g of silica gel using as eluent hexane/ethyl acetate mixtures, containing 2% NEt$_3$. The products were obtained as colorless foams (mixture of diastereoisomers).

N⁶-Benzoyl-9-[5'-O-(4,4'-dimetitoxytrityl)-2'-O-([(triisopropylsilyl)oxy]methyl))-β-D-ribofuranosyl] adenine 3'-[(2-Cyanoethyl) Diisopropylphosphoramidite] (9)

Yield: 90–95%.

TLC: R$_f$ 0.30 (hexane/EtOAc 7:3). $^1$H-NMR (300 MHz, CDCl$_3$): 0.89–1.22 (m, 33H, CH$_3$ from (i-Prop)$_2$N—; CH$_3$ and CH from (i-Prop)$_3$Si—); 2.39 (t, J=6.5, 1H, CH$_2$CN); 2.65 (dt, J=1.2, 6.2, 1H, CH$_2$CN); 3.36 (m, 1H, OCH$_2$); 3.51–3.73 (m, 4H, OCH$_2$, CH from (i-Prop)$_2$N—, H—C(5')); 3.77, 3.78 (2s, 6H, OCH$_3$); 3.84–3.99 (m, 1H, H'—C(5')); 4.37, 4.42 (2m, 1H, H—C(4')); 4.65 (m, 1H, H—C(3')); 4.94–5.02 (m, 2H, OCH$_2$O); 5.24 (m, 1H, H—C(2')); 6.20, 6.23 (2d, J=5.6, 1H, H—C(1')); 6.75–6.81 (m, 4H, arom. H); 7.21–7.61 (m, 12H, arom. H); 7.99–8.04 (m, 2H, arom. H); 8.18, 8.20 (2s, 1H, H—C(2)); 8.69, 8.72 (2s, 1H, H—C(8)); 9.01 (br. s, 1H, NH—C(6)). $^{31}$P-NMR (120 MHz, CDCl$_3$): 150.8, 151.6.

N⁴-Benzoyl-9-[5'-O-(4,4'-dimethoxytrityl)-2'-O-([(tiisopropylsilyl)oxy]methyl))-β-D-ribofuranosyl]cytosine 3'-[(2-Cyanoethyl) Diisopropylphosphoramidite] (10)

Yield: 90–95%.

TLC: R$_f$ 0.50/0.45 (hexane/EtOAc 7:3). $^1$H-NMR (300 MHz, CDCl$_3$): 0.99–1.23 (m, 33H, CH$_3$ from (i-Prop)$_2$N—; CH$_3$ and CH from (i-Prop)$_3$Si—); 2.39 (t, J=6.3, 1H, CH$_2$CN); 2.61 (dt, J=2.5, 6.2, 1H, CH$_2$CN); 3.43–3.97 (m, 12 H, OCH$_2$, CH from (i-Prop)$_2$N—, H and H'-C(5'), OCH$_3$); 4.29–4.56 (m, 3H, H—C(2',3',4')); 5.20 (s, 2H, OCH$_2$O); 6.18, 6.19 (2dt J=2.0, 1H, H—C(1')); 6.84–6.89 (m, 4H, arom. H); 7.26–7.63 (m, 13H, arom. H, H—C(5)); 7.88 (m, 2 H, arom. H); 8.41, 8.51 (2 d, J=7.5, 1H, H—C(6)); 8.40 (br. s, 1H, NH—C(4)). $^{31}$P-NMR (120 MHz, CDCl$_3$): 150.7, 150.9.

N²-Benzoyl-9-[5'-O-(4,4'-dimethoxytrityl)-2'-O-([(triisopropylsilyl)oxy]methyl))-β-D-ribofuranosyl]guanine 3'-[(2-Cyanoethyl) Diisopropylphosphoramidite] (11)

Yield: 90–95%.

TLC: R$_f$ 0.55 (hexane/EtOAc 1:1). $^1$H-NMR (300 MHz, CDCl$_3$): 0.75–1.29 (m, 39H, CH$_3$ from (i-Prop)$_2$N— and (i-Prop)$_2$CHCOO—; CH$_3$ and CH from (i-Prop)$_3$Si—); 1.62, 1.91 (2hept, J=6.9, 1H, CH from (i-Prop)$_2$CHCOO—); 2.26, (t, J=6.6, 1H, CH$_2$CN); 2.74 (dt, J=1.1, 6.8, 1H; CH$_2$CN); 3.19 (m, 1H, OCH$_2$); 3.45–3.69 (m, 3H, CH from (i-Prop)$_2$N—, OCH$_2$); 3.756, 3.761, 3.765 (3s, 6H, OCH$_3$); 3.88–4.17 (m, 2H, H,H'—C(5')); 4.22, 4.32 (2br. s, 1H, H—C(4')); 4.58 (m, 1H, H—C(3')); 4.89–4.98 (m, 2H, OCH$_2$O); 5.07, 5.16 (2d, J=4.7, 7.6, 1H, H—C(2')); 5.84, 5.96 (2d, J=7.6, 1H, H—C(1')); 6.76–6.81 (m, 4H, arom. H); 7.21–7.55 (m, 9H, arom. H); 7.74, 7.79 (2s, 1H, H—C(8)); 7.87, 8.26 (2br. s, 1H, NH—C(2)); 11.97 (br. s, 1H, H—N(1)). $^{31}$P-NMR (120 MHz, CDCl$_3$): 150.4, 150.7.

1-[5'-O-(4,4'-dimethoxytrityl)-2-O-([(triisopropylsilyl)oxy]methyl))-β-D-ribofuranosyl]uracicle 3'-[(2-Cyanoethyl) Diisopropylphosphoramidite] (12)

Yield: 90–95%

TLC: R$_f$ 0.50 (hexane/EtOAc 7:3). $^1$H-NMR (300 MHz, CDCl$_3$): 1.02–1.18 (m, 33H, CH$_3$ from (i-Prop)$_2$N—; CH$_3$ and CH from (i-Prop)$_3$Si—); 2.39 (t, J=6.6, 1H, CH$_2$CN); 2.53 (m, 1H, OCH$_2$); 2.64 (dt, J=1.5, 6.2, 1H, CH$_2$CN); 3.39 (m, 1H, OCH$_2$); 3.52–3.69 (m, 3.5H, CH from (i-Prop)$_2$N—, H,H'—C(5')); 3.78, 3.79, 3.80 (3s, 6H, OCH$_3$); 3.82–3.96 (m, 0.5H, H'—C(5')); 4.19, 4.27 (2br. s, 1H, H—C(4')); 4.39–4.49 (m, 2H, H—C(2',3')); 4.98–5.07 (m, 2H, OCH$_2$O); 5.32, 5.36 (2d, J=8.1, 1H, H—C(5)); 6.12 (d, J=4.4, 0.5H, H—C(1')); 6.13 (d, J=4.2, 0.5H, H—C(1')); 6.81–6.86 (m, 4H, arom. H); 7.23–7.43 (m, 9H, arom. H); 7.81, 7.86 (2d, J=8. 1, 1H, H—C(6)); 8.75 (hr. s, 1H, H—N(2)). $^{31}$P-NMR (120 MHz, CDCl$_3$): 150.9, 151.3.

EXAMPLE 6

Procedure for the synthesis of ribonucleic acids with Phosphoramidites 9–12

In a typical synthesis, commercially available "Controlled Pore Glass" supports loaded with 2 μmoles of the appropriately protected ribonucleosides (from Sigma) were used on a DNA-synthesizer (Pharmacia Gene Assembler). The original protocol of the manufacturer [10], developed for the synthesis of DNA-oligonucleotides in a 1.3 μmol scale, was used with the following exceptions: For each coupling 0.16 ml of a 0.08 M (=1.28 μmoles) phosphoramidite solution was employed and the coupling time was adjusted to 12 minutes. Typical coupling yields determined by the built-in detritylation assay were 98.6–99.1% per step.

Figure 1:
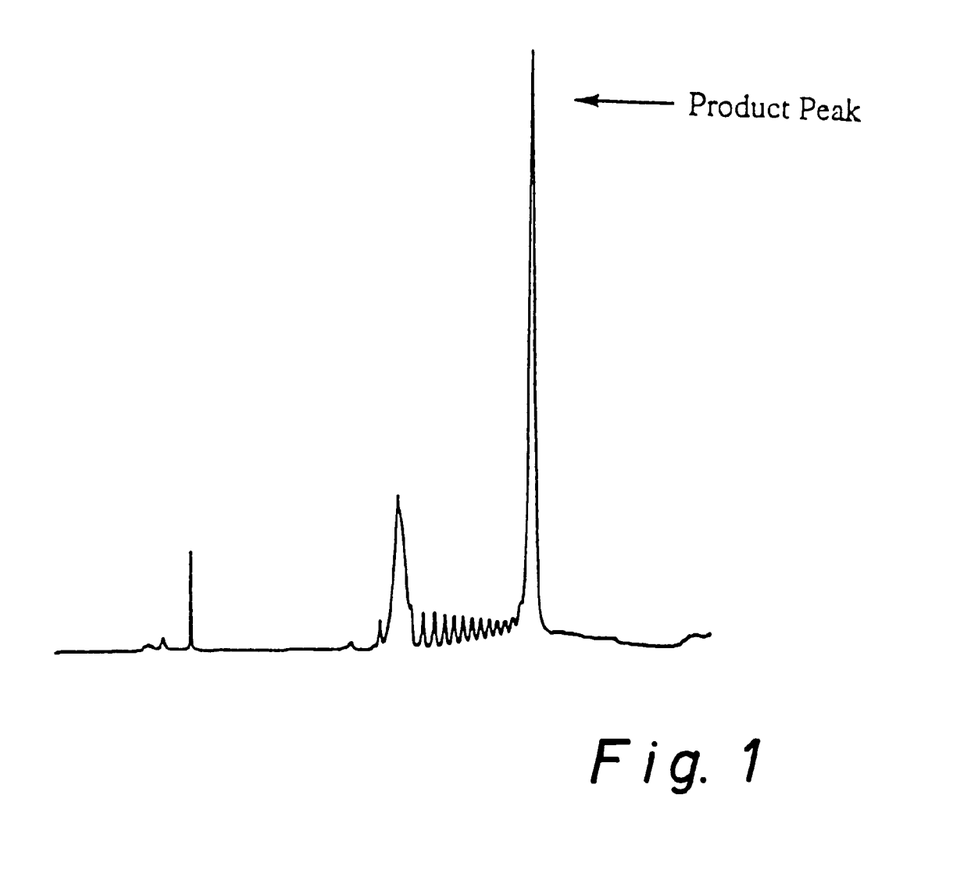
FIG. 1 and FIG. 2 show HPLC-traces of crude oligoribonucleotides obtained from phosphoramidites according to the invention.
Figure 2:
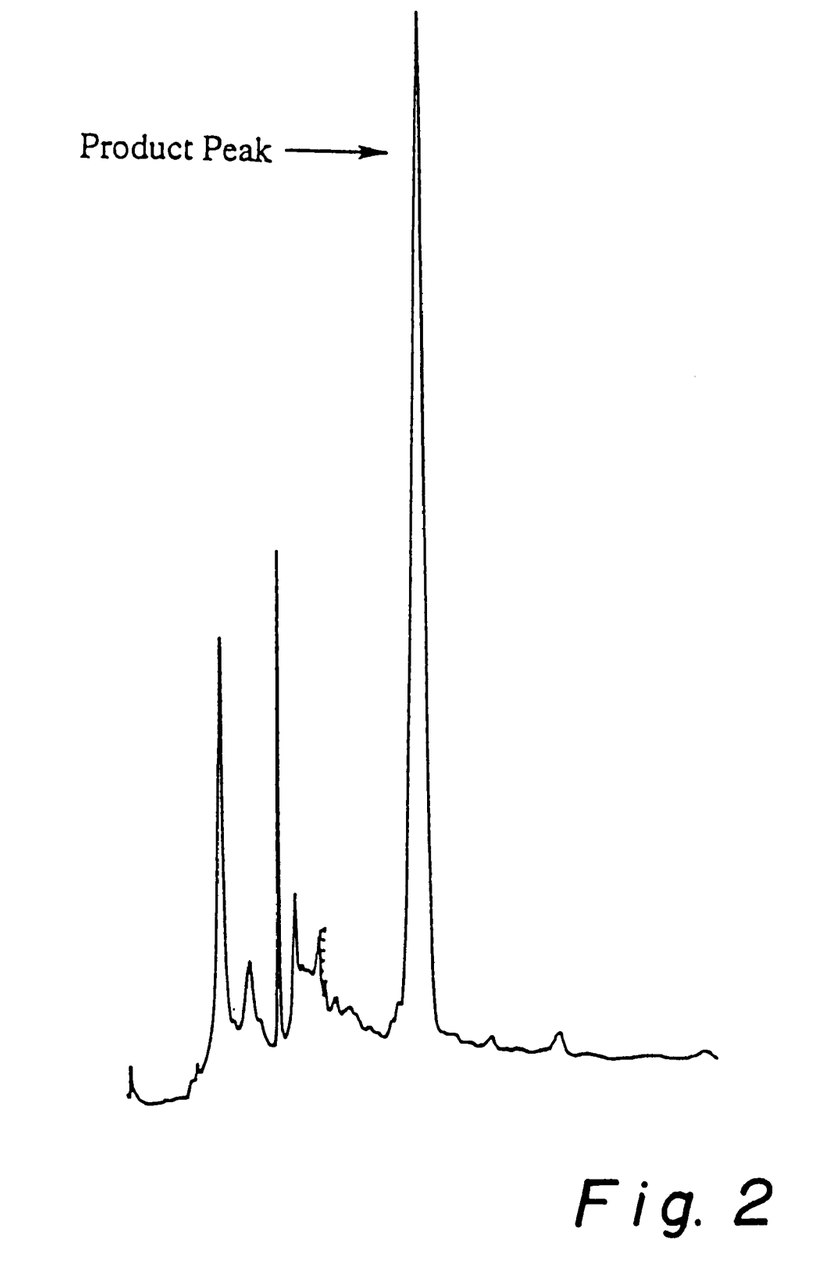

HPLC Traces of crude oligoribonucleotides obtained from posphoramidites 9 to 12 are shown in the following FIGS. 1 and 2. The parameters used for the preparation were as follows:

1 10M $CH_3NH_2$ in $H_2O$/EtOH 1:1; 25° C., 5 hours 2 1M Tetrabutylammonium fluoride in THF; 25° C., 5 hours 3 chromatography on reversed phase columns The sequence r(UUUUUUUUUUUUUUUUUUUU) (FIG. 1) was produced with an overall coupling yield of 78%, the sequence r(GCUCGUCUGAUGAGUCCGUGAGGACGAAAGACCGU) (FIG. 2) with an overall coupling yield of 65%.

LITERATURE

[1] B. E. Griffin, M. Jarman, C. B. Reese, Tetrahedron 1968, 24, 639; D. G. Norman, C. B. Reese, H. T. Serafinowska, Tetrahedron Lett. 1984, 25, 3015; C. B. Reese, R. Saffhill, J. E. Sulston, Tetrahedron 1970, 26, 1023; M. V. Rao, C. B. Reese, V. Schehlman, P.-S. Y. Chen, Chem. Soc. Perk. Trans. 1, 1993, 43; D. C. Capaldi, C. B. Reese, Nucleic Acids Res. 1994, 22, 2209; M. V. Rao, P. Macfarlane, Nucleos. Nucleot. 1995, 14, 911.

[2] M. E. Schwartz, R. R. Breaker, G. T. Asteriadis, J. S. deBear, G. R. Gough, Bioorg. Med. Chem. Lett. 1992, 2, 1019; S. Pitsch, Helv. Chimn. Acta 1997, in preparation.

[3] K. K. Ogilvie, K. L. Sadana, E. A. Thompson, M. A. Quilliam, J. B. Westmore, Tetrahedron Lett. 1974, 15, 2861; K. K. Ogilvie, S. L. Beaucage, A. L. Schifman, N. Y. Theriault, K. L. Sadana, Can. J. Chem. 1978, 56, 2768; D. Flockerzi, G. Silber, R. Charubala, W. Schlosser, R. S. Varma, F. Creegan, Liebigs Ann. Chem. 1981, 1568; N. Usman, K. K. Ogilvie, M.-Y. Jiang, R. J. Cedergren, J. Am. Chem. Soc. 1987, 109, 7845; K. K. Ogilvie, N. Usman, K Nicoghosian, R. J. Cedergren, Proc. Natl. Acad. Sci. U.S.A. 1988, 85, 5764.

[4] N. D. Sinha, J. Biernat, H. Koster, Tetrahedron Lett. 1983, 24, 5843; N. D. Sinha, J. Biernat, J. McManus, H. Koster, Nucleic Acids Res. 1984, 12, 4539.

[5] M. D. Matteucci, M. H. Caruthers, Tetrahedron Lett. 1980, 21, 3243; M. D. Matteucci, M. H. Caruthers, J. Am. Chem. Soc. 1981, 3185; S. L. Beaucage, M. H. Caruthers M. H., Tetrahedron Lett. 1981, 22, 1859; L. J. McBride, M. H. Caruthers, ibid. 1983, 24, 245; R. L. Letsinger, K. K. Ogilvie, J. Am. Chem. Soc. 1969, 91, 3350.

[6] S. J. Jones and C. B. Reese, J. Chem. Soc. Perkin I, 1979 2762.

[7] N. Usman, K. K Ofilvie, M. Y. Jiang amd R. L. Cedergren, J. Am. Chem. Soc., 109, 7845.

[8] L.-L. Gundersen, T. Benneche, K. Undheim, Acta Chem. Scand. 1989, 43, 706.

[9] G. H. Hakimelahi, Z. A. Proba, K. K. Ogilvie, Can. J. Chem. 1982, 60, 1106.

[10] Pharmacia, 'User Manual for Gene Assembler Plus'.

We claim:

1. A ribonucleoside-derivative of the formula wherein
R$^1$ is a base of the purine- or pyrimidine-family or a derivative of such a base;
R$^2$ is a proton or wherein
R$^7$ and R$^8$ are optionally substituted alkyl- or aryl- groups which are optionally cyclically connected to each other, and
R$^9$ is an optionally substituted alkyl- or aryl-group;
R$^3$ is a proton or a protection group; and
X is where
R$^4$, R$^5$ and R$^6$ are the same or different and are optionally substituted alkyl or aryl groups which are optionally connected to each other to form a ring.

2. The ribonucleoside-derivative according to claim 1, wherein R$^4$, R$^5$, and R$^6$ are alkyl- or aryl-substituents which together contain between six and thirty carbon atoms.

3. The ribonucleoside-derivative according to claim 2, wherein R$^4$, R$^5$, and R$^6$ are optionally aryl-substituted alkyl-groups or alkyl-substituted aryl-groups.

4. The ribonucleoside-derivative according to claim 2, wherein R$^4$, R$^5$, and R$^6$ are optionally substituted with heteroatoms.

5. The ribonucleoside-derivative according to claim 2, wherein R$^4$, R$^5$, and R$^6$ are optionally cyclically connected to each other.

6. The ribonucleoside-derivative according to claim 2, wherein R$^4$, R$^5$, and R$^6$ are isopropyl-groups.

7. The ribonucleoside-derivative according to claim 1, wherein R$^1$ is selected from the group consisting of a substituent moiety derived from cytosine, guanine, adenine, uracil and thymine.

8. The ribonucleoside-derivative according to claim 1, characterized, in that wherein R$^1$ is substituted with an N-acyl protecting group.

9. The ribonucleoside-derivative according to claim 1, wherein R$^2$ is

10. The ribonucleoside-derivative according to claim 9, wherein R$^9$ is a 2-cyanoethyl-group and R$^7$ and R$^8$ are isopropyl groups.

11. The ribonucleoside-derivative according to claim 1, wherein R$^3$ is selected from the group consisting of a monomethoxytrityl- and a dimethoxytrityl-group.

12. A method for the chemical synthesis of an RNA-oligonucleotide with a predetermined nucleotide-sequence comprising coupling a ribonucleoside-derivative of claim 1, wherein R$^2$ is a phosphoramidite, with a terminally deprotected RNA precursor.

13. A method for the preparation of a ribonucleoside-derivative according to claim 1, comprising
reacting a nucleoside of the formula where R$^1$ and R$^2$ are as defined in claim 1,
with a dialkyl or diaryl tin compound under alkaline conditions in the presence of an excess of a tertiary amine to produce a 2',3'-di-O-dialkyl-(or diaryl-)stannyl derivative of said nucleoside, and
reacting said stannyl derivative with a silyloxymethylhalogenide of the formula where Y is halogen.

14. A method according to claim 13, further comprising substituting the oxygen in the 3'-position of said ribonucleoside-derivative.

* * * * *